(12) United States Patent
Vann, III

(10) Patent No.: US 11,382,321 B1
(45) Date of Patent: Jul. 12, 2022

(54) LIVE BAIT CONTAINER ASSEMBLIES

(71) Applicant: Marvin E. Vann, III, Haughton, LA (US)

(72) Inventor: Marvin E. Vann, III, Haughton, LA (US)

(*) Notice: Subject to any disclaimer, the term of this patent is extended or adjusted under 35 U.S.C. 154(b) by 525 days.

(21) Appl. No.: 16/253,057

(22) Filed: Jan. 21, 2019

(51) Int. Cl.
*A01K 97/04* (2006.01)
*A01K 67/033* (2006.01)
*B63B 17/00* (2006.01)

(52) U.S. Cl.
CPC ............ *A01K 97/04* (2013.01); *A01K 67/033* (2013.01); *A01K 67/0332* (2013.01); *B63B 17/00* (2013.01)

(58) Field of Classification Search
CPC .. A01K 97/04; A01K 67/0332; A01K 67/033; B63B 17/00
USPC .......................................................... 43/55
See application file for complete search history.

(56) References Cited

U.S. PATENT DOCUMENTS

| | | | |
|---|---|---|---|
| 2,631,807 A | 3/1953 | Witt | |
| 3,039,224 A | 6/1962 | Hartzog | |
| 3,315,402 A * | 4/1967 | Scott | A01K 97/04 43/55 |
| 5,163,648 A | 11/1992 | Schneider | |
| 5,799,435 A | 9/1998 | Stafford | |
| 5,813,646 A * | 9/1998 | Bartholomae | B63B 29/06 248/230.7 |
| 6,421,951 B1 | 7/2002 | Kuhl | |
| 6,442,887 B2 | 9/2002 | Sanquist | |
| 9,345,238 B1 | 5/2016 | Higginbotham | |
| 10,059,407 B1 * | 8/2018 | Ingalls | B63B 17/02 |
| 10,731,919 B1 * | 8/2020 | Gutierrez | F25D 27/005 |

(Continued)

OTHER PUBLICATIONS

"Millennium Shadetree", Apr. 26, 2018, retrieved from https://www.youtube.com/watch?v=YjujHAGF-Mg on Jun. 3, 2021 (Year: 2018).*

*Primary Examiner* — Peter M Poon
*Assistant Examiner* — Mohamed Aboukoura
(74) *Attorney, Agent, or Firm* — R. Keith Harrison

(57) ABSTRACT

Live bait container assemblies for mounting on a seat pedestal of a watercraft seat on a watercraft may include a bait container having a container bottom panel. A plurality of container corners may be carried by the container bottom panel. A plurality of recessed container side panels may extend between the plurality of container corners. A plurality of container handles may extend between the plurality of container corners in spaced-apart relationship to the plurality of recessed container side panels, respectively. A container top panel may be carried by the plurality of container corners and the plurality of recessed container side panels. A container interior may be formed by the container bottom panel, the plurality of container corners, the plurality of recessed container side panels and the container top panel. A container neck having a neck opening may extend from the container top panel in communication with the container interior. A container lid assembly may be removably carried by the container neck and closing the neck opening. The container lid assembly may include a container lid rim detachably carried by the container neck, a dish-shaped inner lid portion detachably carried by the container lid rim and a container lid handle carried by the inner lid portion. Container lid assemblies for a container are also disclosed.

18 Claims, 17 Drawing Sheets

(56) References Cited

U.S. PATENT DOCUMENTS

| | | | |
|---|---|---|---|
| 2009/0064565 A1* | 3/2009 | Sloop | A01K 97/05 43/57 |
| 2009/0223114 A1* | 9/2009 | Obrien | A01M 23/02 43/100 |
| 2015/0289494 A1 | 10/2015 | Davis | |
| 2016/0120163 A1* | 5/2016 | Arden | A01K 97/05 43/57 |
| 2017/0225752 A1* | 8/2017 | O'Neal | B63B 29/06 |
| 2018/0020651 A1* | 1/2018 | Larkin | B63B 25/002 43/21.2 |
| 2018/0110335 A1* | 4/2018 | O'Hagan | B63B 29/04 |
| 2019/0118908 A1* | 4/2019 | Hernandez | A45B 11/00 |
| 2020/0120914 A1* | 4/2020 | Gniffke | A01K 97/05 |

\* cited by examiner

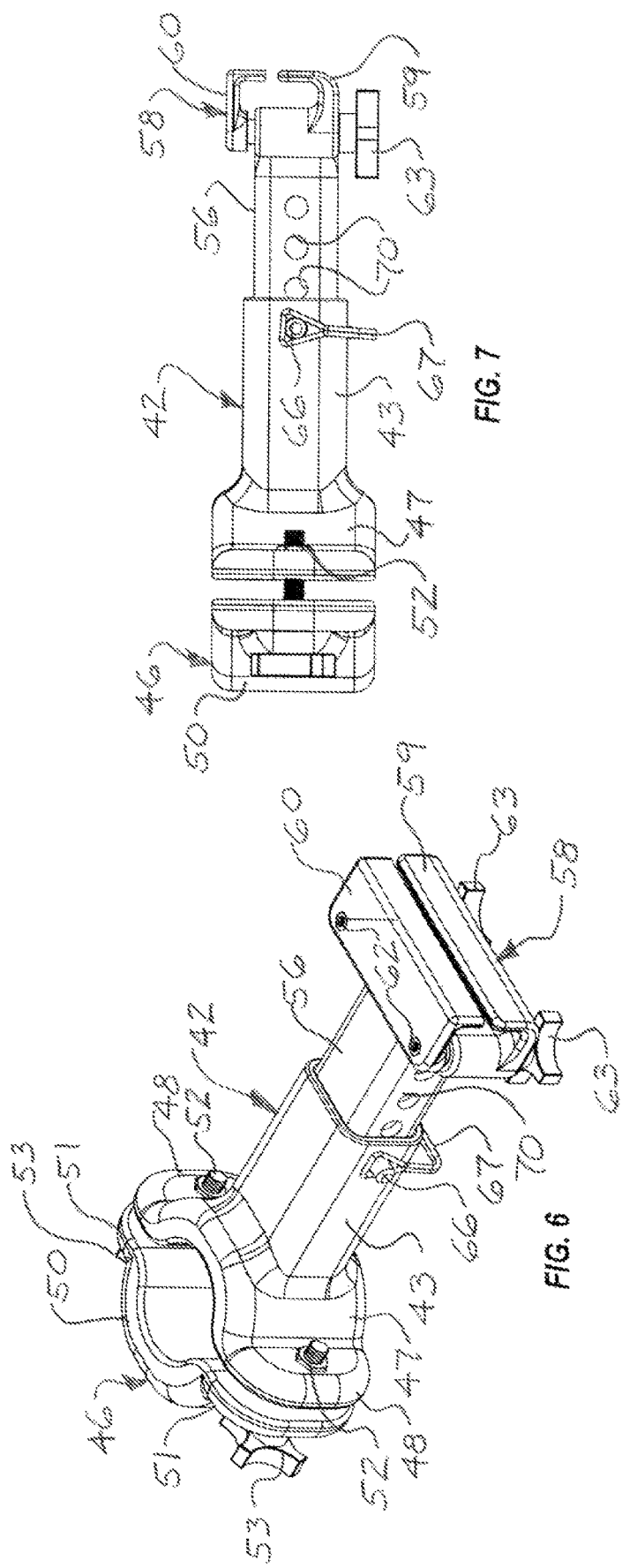

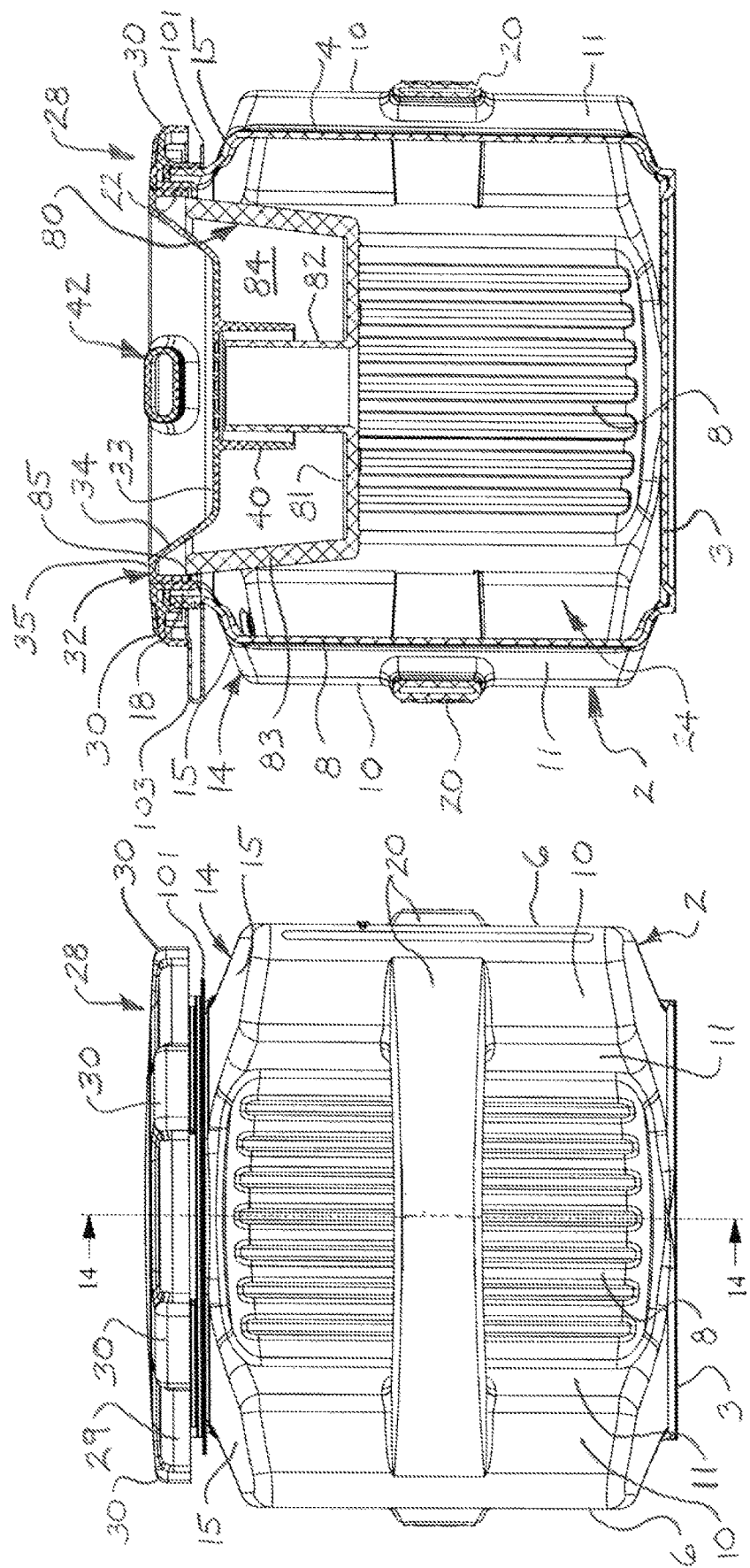

US 11,382,321 B1

LIVE BAIT CONTAINER ASSEMBLIES

FIELD

Illustrative embodiments of the disclosure generally relate to bait containers for holding live bait. More particularly, illustrative embodiments of the disclosure relate to live bait container assemblies which can be secured to a seat pedestal of a watercraft seat to hold live bait in a position which is accessible to a user sitting in the seat.

SUMMARY

Illustrative embodiments of the disclosure are generally directed to live bait container assemblies for mounting on a seat pedestal of a watercraft seat on a watercraft. An illustrative embodiment of the live bait container assemblies may include a bait container having a container bottom panel. A plurality of container corners may be carried by the container bottom panel. A plurality of recessed container side panels may extend between the plurality of container corners. A plurality of container handles may extend between the plurality of container corners in spaced-apart relationship to the plurality of recessed container side panels, respectively. A container top panel may be carried by the plurality of container corners and the plurality of recessed container side panels. A container interior may be formed by the container bottom panel, the plurality of container corners, the plurality of recessed container side panels and the container top panel. A container neck having a neck opening may extend from the container top panel in communication with the container interior. A container lid assembly may be removably carried by the container neck and closing the neck opening. The container lid assembly may include a container lid rim detachably carried by the container neck, a dish-shaped inner lid portion detachably carried by the container lid rim and a container lid handle carried by the inner lid portion.

Illustrative embodiments of the disclosure are further generally directed to container lid assemblies for removable attachment to a container. An illustrative embodiment of the container lid assemblies includes a container lid rim configured to detachably engage the container. A dish-shaped inner lid portion may be removably fitted into the container lid rim. The inner lid portion may include a bottom lid wall. A side lid wall may angle from the bottom lid wall. A lid flange may extend from the side lid wall. The lid flange may be configured for removably engaging the container lid rim. A container lid handle may span the side lid wall. At least one container lid opening may be provided in the bottom lid wall. A lid baffle may extend from the bottom lid wall. The lid baffle may circumscribe the at least one container lid opening.

BRIEF DESCRIPTION OF THE DRAWINGS

Illustrative embodiments of the disclosure will now be described, byway of example, with reference to the accompanying drawings, in which:

FIG. 6 is a right front perspective view of a typical arm assembly of the illustrative live bait container assembly;

FIG. 7 is a right side view of the arm assembly;

FIG. 13 is a rear view of the bait container with the container lid assembly in the closed position and with the worm insert (not illustrated) deployed in place therein;

FIG. 14 is a cross-sectional view, taken along section lines 14-14 in FIG. 13, of the bait container with the worm insert deployed in place therein;

DETAILED DESCRIPTION

The following detailed description is merely exemplary in nature and is not intended to limit the described embodiments or the application and uses of the described embodiments. As used herein, the word "exemplary" or "illustrative" means "serving as an example, instance, or illustration." Any implementation described herein as "exemplary" or "illustrative" is not necessarily to be construed as preferred or advantageous over other implementations. All of the implementations described below are exemplary implementations provided to enable persons skilled in the art to make or use the embodiments of the disclosure and are not intended to limit the scope of the disclosure, which is defined by the claims. For purposes of description herein, the terms "upper", "lower", "left", "rear", "right", "front", "vertical", "horizontal", and derivatives thereof shall relate to the invention as oriented in FIG. 1. Furthermore, there is no intention to be bound by any expressed or implied theory presented in the preceding technical field, background, brief summary or the following detailed description. It is also to be understood that the specific devices and processes illustrated in the attached drawings, and described in the following specification, are simply exemplary embodiments of the inventive concepts defined in the appended claims. Hence, specific dimensions and other physical characteristics relating to the embodiments disclosed herein are not to be considered as limiting, unless the claims expressly state otherwise.

Figure 21:
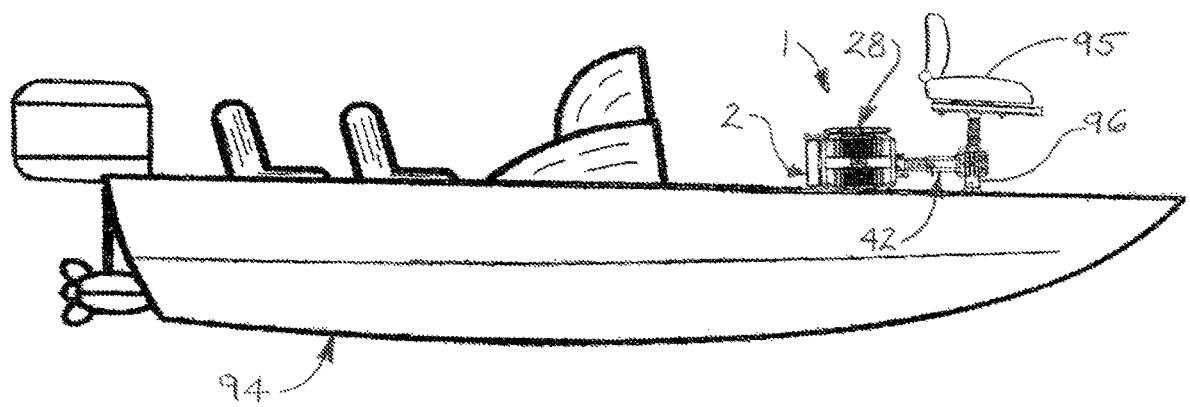
FIG. 21 is a side view of a typical watercraft with a watercraft seat on the watercraft and an illustrative embodiment of the live bait container assembly mounted on a seat pedestal of the watercraft seat.
Figure 22:
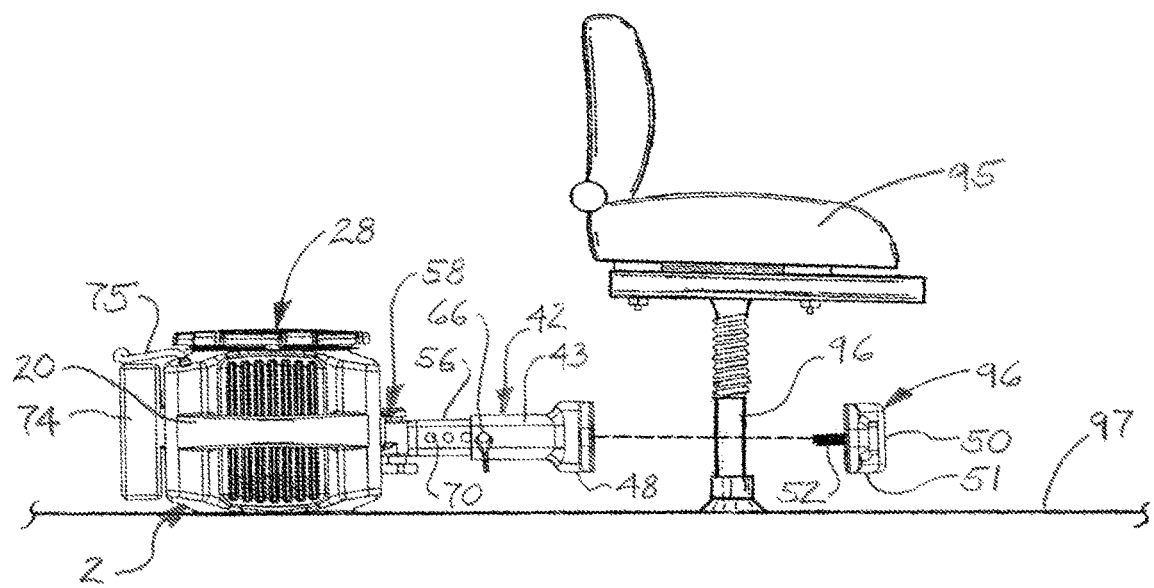
FIG. 22 is an exploded side view illustrating typical attachment of the live bait container assembly to the seat pedestal.
Figure 23:
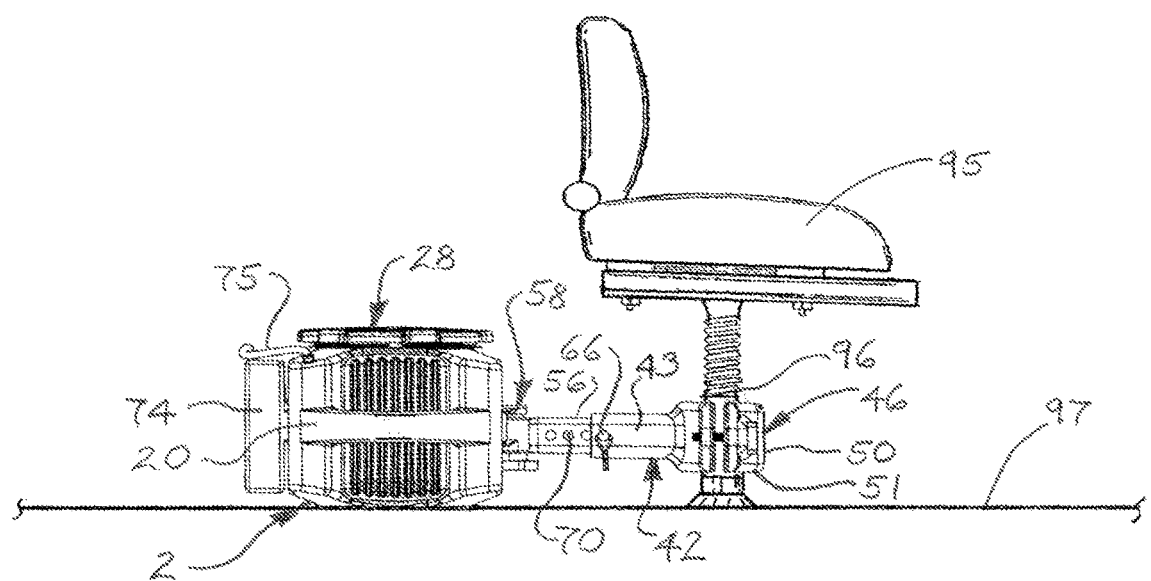
FIG. 23 is a side view of the live bait container assembly attached to the seat pedestal.

Referring initially to FIGS. 21-23 of the drawings, an illustrative embodiment of the live bait container assemblies, hereinafter assembly, is generally indicated by reference numeral 1. The assembly 1 may include a bait container 2. An arm assembly 42 may extend from the bait container 2. In typical application of the assembly 1, which will be hereinafter described, a supply of live bait (not illustrated) such as worms, crickets and/or a supply of water with minnows, for example and without limitation, may be placed in the bait container 2. The arm assembly 42 may be attached to a seat pedestal % of a watercraft seat 95 on a watercraft 94. The arm assembly 42 may hold or secure the bait container 2 on the watercraft floor 97 (FIGS. 22 and 23) of the watercraft 94 and in front of, next to or behind the watercraft seat 95. Accordingly, a user (not illustrated) may sit in the seat 95 and easily access the live bait in the bait container 2 typically for fishing purposes. Alternatively, in some applications, the bait container 2 may be selectively detached from the arm assembly 42 as the arm assembly 42 typically remains attached to the seat pedestal % and the bait container 2 carried by the user from the watercraft 94 or to different locations or positions on the watercraft 94.

Referring next to FIGS. 1-12 of the drawings, in some embodiments, the bait container 1 may have a generally rectangular, square-shaped or cubed configuration, as illustrated. In alternative embodiments, the bait container 1 may have a triangular, pentagonal, hexagonal or other polygonal shape or may alternatively have a round, oval or elliptical shape. In some embodiments, the bait container 2 may be molded, casted, machined and/or otherwise fabricated of plastic, composites, metals and/or other suitable materials. In some embodiments, the bait container 2 may include one or more transparent or translucent materials. The bait container 2 may be fabricated in one piece using conventional molding techniques or may be fabricated in multiple pieces and assembled using brackets, clamps, mechanical fasteners and/or other suitable assembly techniques known by those skilled in the art.

Figure 5:
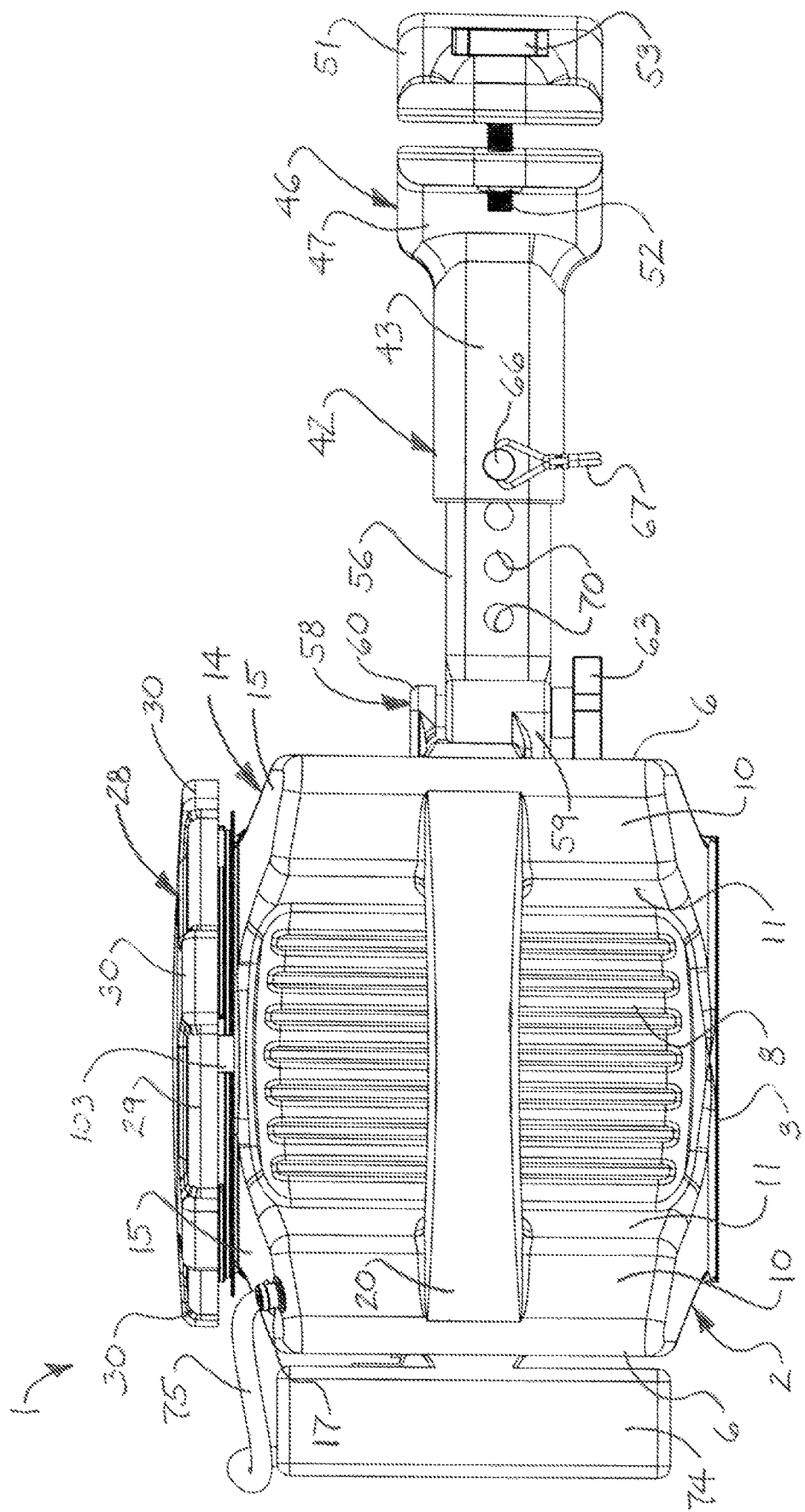
FIG. 5 is a left side view of the illustrative live bait container assembly.

As illustrated in FIG. 5, the bait container 2 may include a flat or planar container bottom panel 3. In some embodiments, multiple container corners 6 may extend upwardly from the container bottom panel 3 at respective corners of the bait container 2. Container side panels 8 may extend between the adjacent container corners 6. The container side panels 8 may at least partially define the respective faces of the bait container 2. In some embodiments, the container side panels 8 may be recessed relative to the container corners 6 for purposes which will be hereinafter described. Accordingly, a pair of corner side panels 10 may extend from each container corner 6. In some embodiments, the corner side panels 10 may be disposed at about a perpendicular or 90-degree angle to each other. A pair of beveled corner panels 11 may angle inwardly from the respective corner side panels 10. Each container side panel 8 may extend between the beveled corner panels 11 at each face of the bait container 2. Thus, each face of the bait container 2 may include a pair of the corner side panels 10 extending from the respective container corners 6, a pair of the beveled corner panels 11 extending from the respective corner side panels 10 and the container side panel 8 extending between the beveled corner panels 11. Accordingly, the beveled corner panels 11 may recess each container side panel 8 relative to the corner side panels 10 on each corresponding face of the bait container 2.

In some embodiments, a maximum fill line 26 may be provided on the bait container 2 to mark the maximum desired water fill level of the water contained in the container interior 24. The maximum till line 26 may be provided on one of the container corners 6, as illustrated, and/or in any other suitable location on the bait container 2.

Multiple container handles 20 may be provided on the bait container 2. In some embodiments, the container handles 20 may be provided on the respective faces of the bait container 2. Each container handle 20 may extend between each corresponding pair of adjacent container corners 6. Each container handle 20 may be disposed in spaced-apart relationship to the corresponding recessed container side panel 8 on each corresponding face of the bait container 2. In some embodiments, each container handle 20 may be molded or otherwise fabricated in one piece with the corner side panels 10 on each corresponding side or face of the bait container 2. In other embodiments, the container handles 20 may be fabricated separately and attached to the bait container 2 using a suitable attachment technique known by those skilled in the art.

In typical application of the assembly 1, which will be hereinafter described, the container handles 20 may enable a user to grip and hand-carry the bait container 2. The container handles 20 may additionally facilitate attachment of the arm assembly 42 to the bait container 2. In some applications, the container handles 20 may facilitate attachment of an aerator 74 to the bait container 2 and well as various accessories (not illustrated) such as a worm light, a dry box for a cell phone or wallet, a fishing rod holder or a shoulder strap or securing strap, for example and without limitation. In some applications, at least one accessory may be attached to each container handle 20 on each corresponding face of the bait container 2.

A container top panel 14 may be provided on the container corners 6, the container side panels 8, the corner side panels 10 and the beveled corner panels 11. In some embodiments, the container top panel 14 may include container panel portions 15 which extend over each corresponding container corner 6 with its corner side panels 10 and beveled corner panels 11. In some embodiments, the width, or distance between adjacent ones of the container corners 6, may be greater than the height, or distance between the container bottom panel 3 and the container top panel 14, of the bait container 2. This expedient may impart a low center of gravity to the bait container 2 and render the bait container 2 stable and resistant to turning over on the watercraft floor 97 of the watercraft 94.

Figure 9:
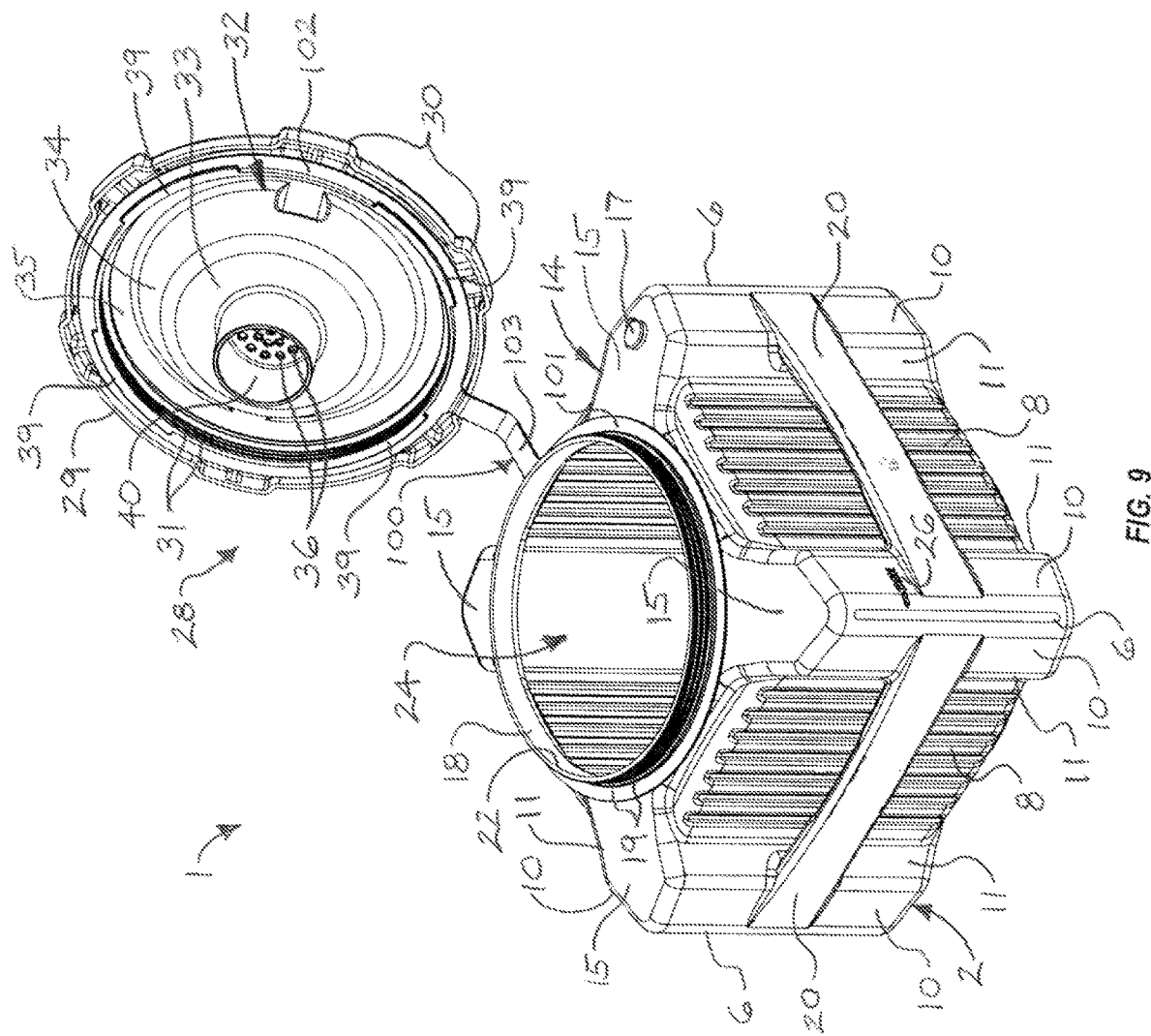
FIG. 9 is a perspective view of the bait container with the container lid assembly shown in an open position on the bait container.
Figure 10:
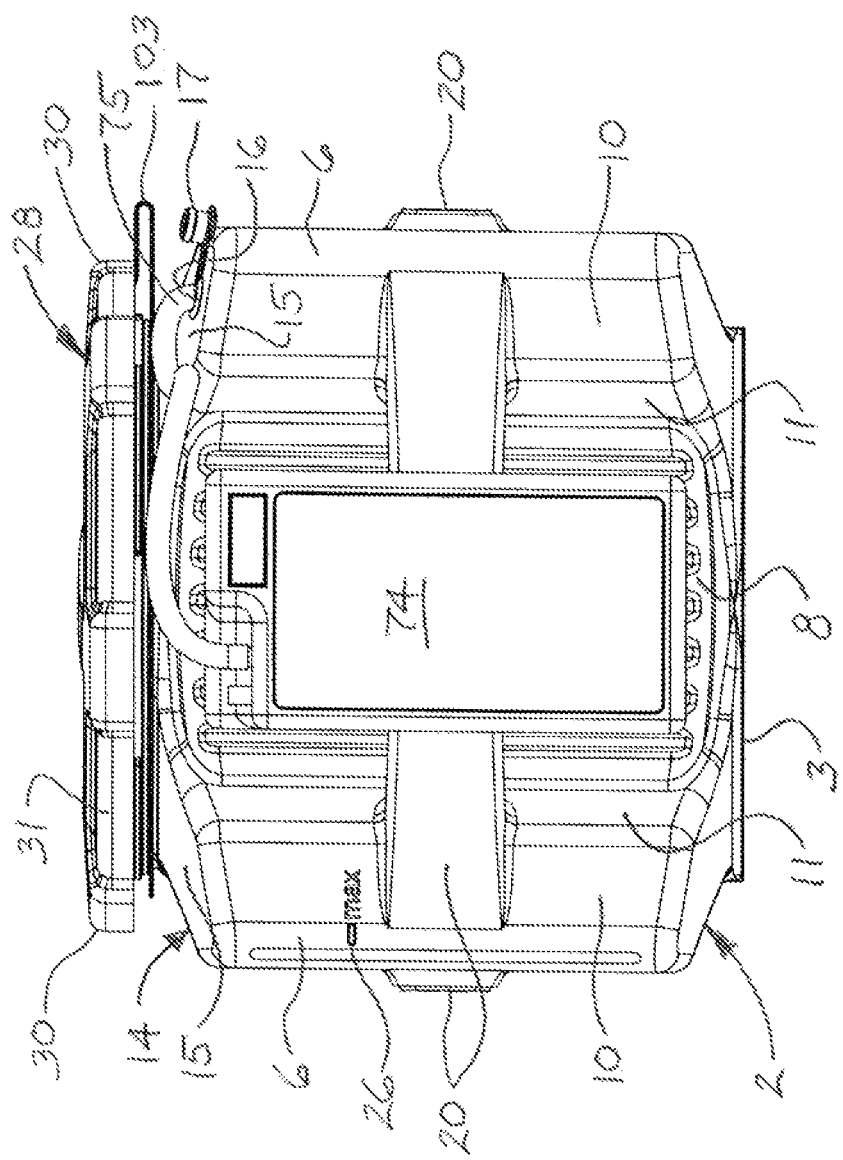
FIG. 10 is a front view of the bait container with an aerator mounted on the bait container and an aerator tube extending from the aerator and inserted in an aerator opening in the bait container.
Figure 11:
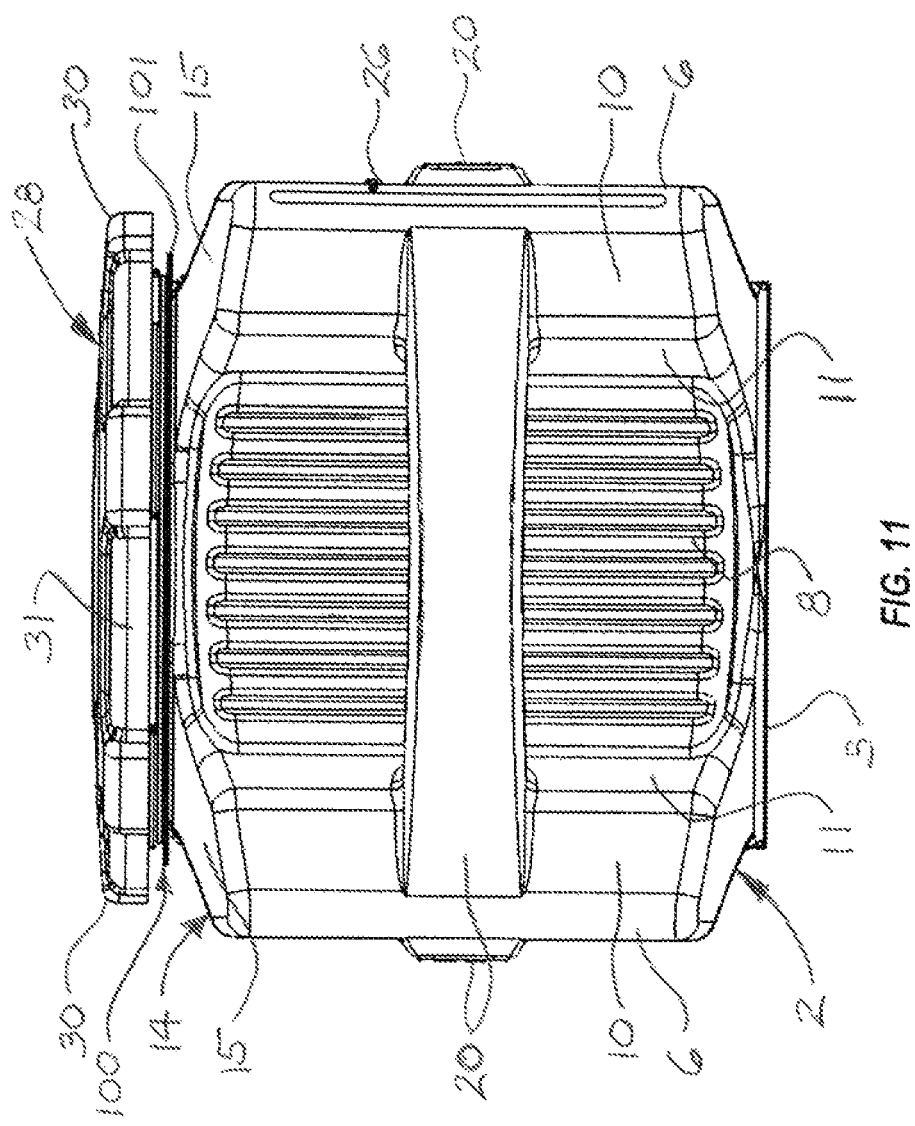
FIG. 11 is a rear view of the bait container.

As illustrated in FIG. 9, a container interior 24 may be formed by and between the container bottom panel 3, the container corners 6, the corner side panels 10, the beveled corner panels 11, the container side panels 8 and the container top panel 14. A container neck 18 may extend from the container top panel 14. The container neck 18 may have a neck opening 22 which communicates with the container interior 24. In some embodiments, exterior container neck threads 19 may be provided on the container neck 18 for purposes which will be hereinafter described.

Figure 1:
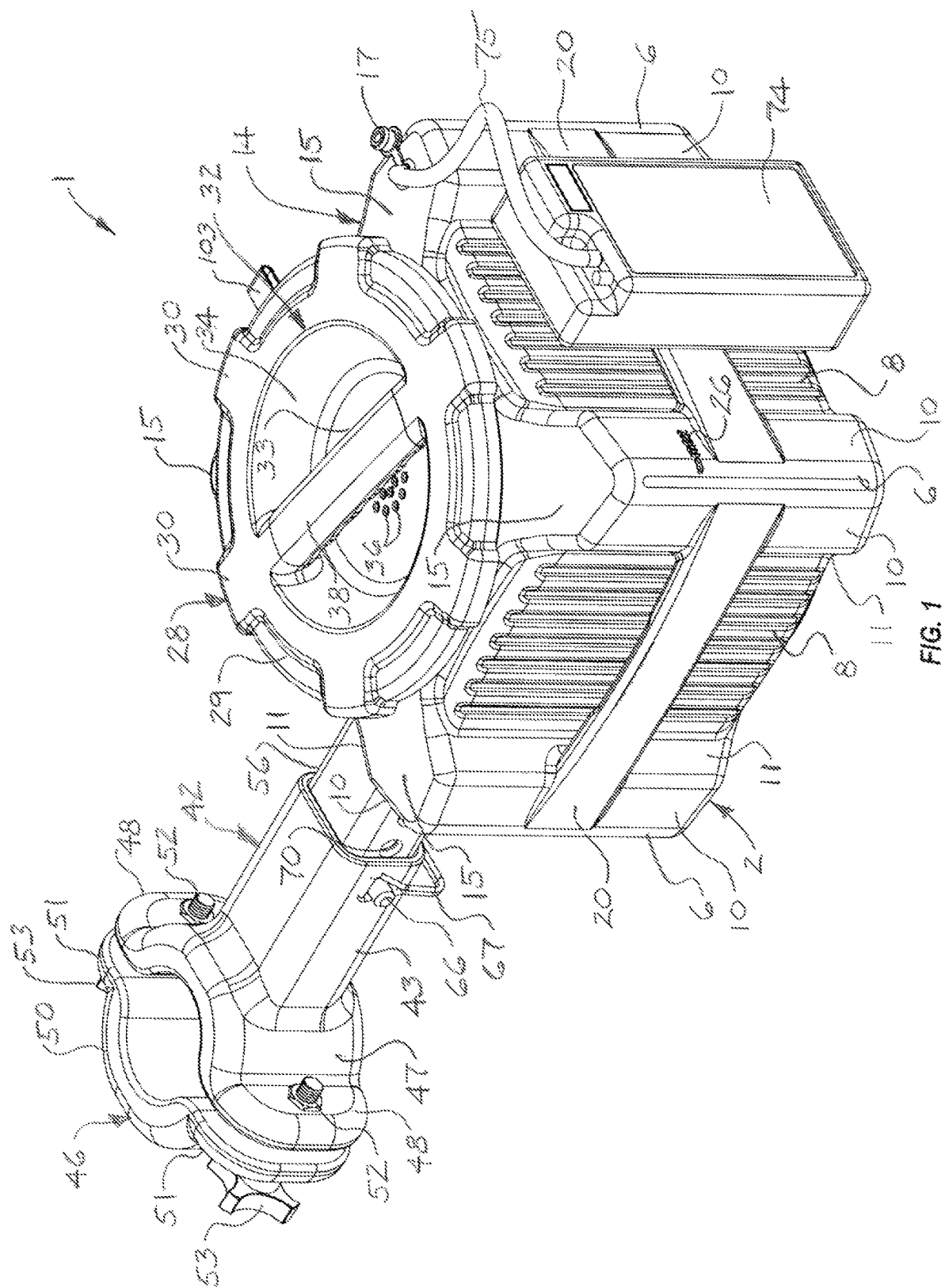
FIG. 1 is a right front perspective view of an illustrative embodiment of the live bait container assemblies.
Figure 2:
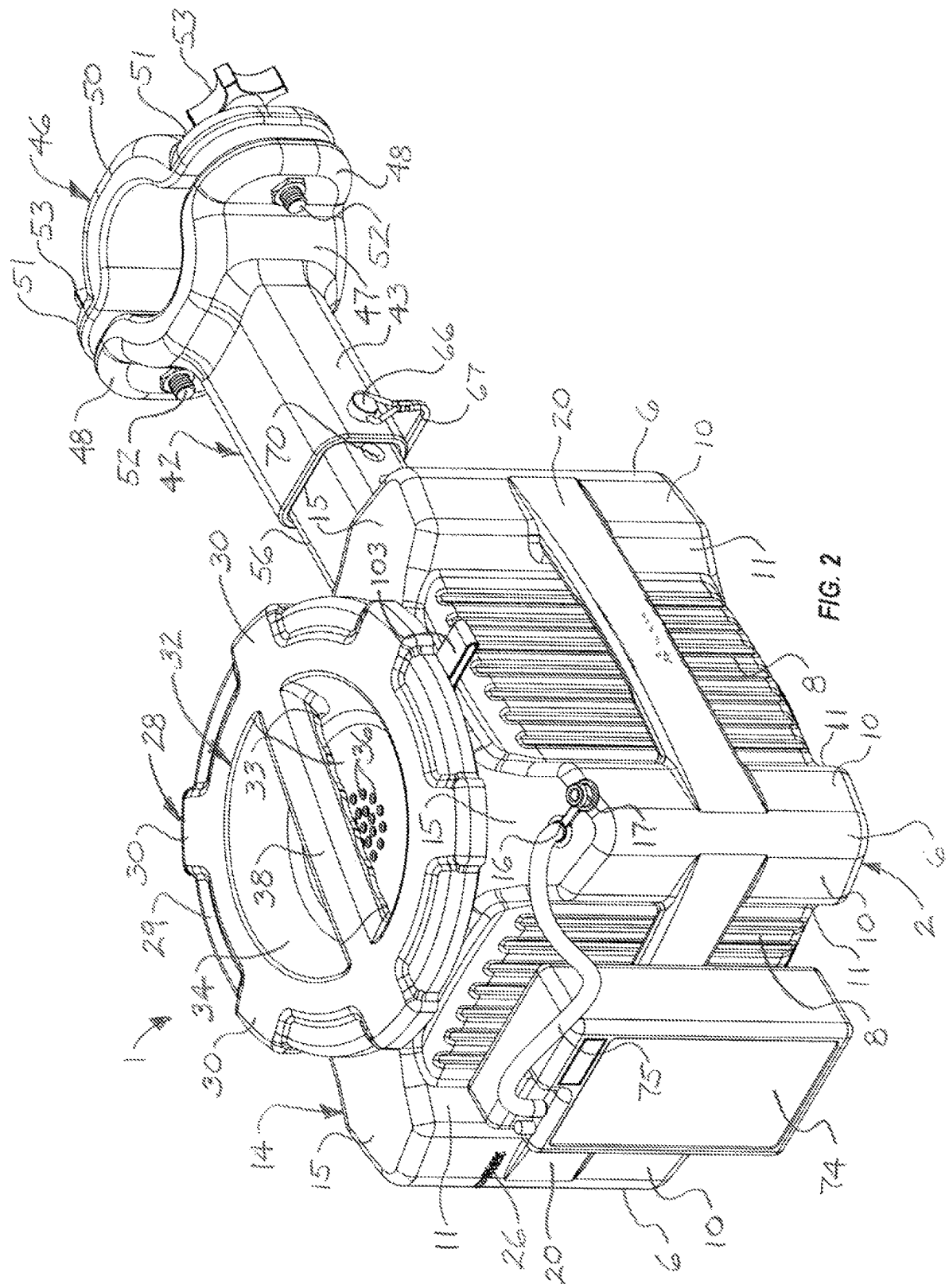
FIG. 2 is a left front perspective view of the illustrative live bait container assembly.
Figure 3:
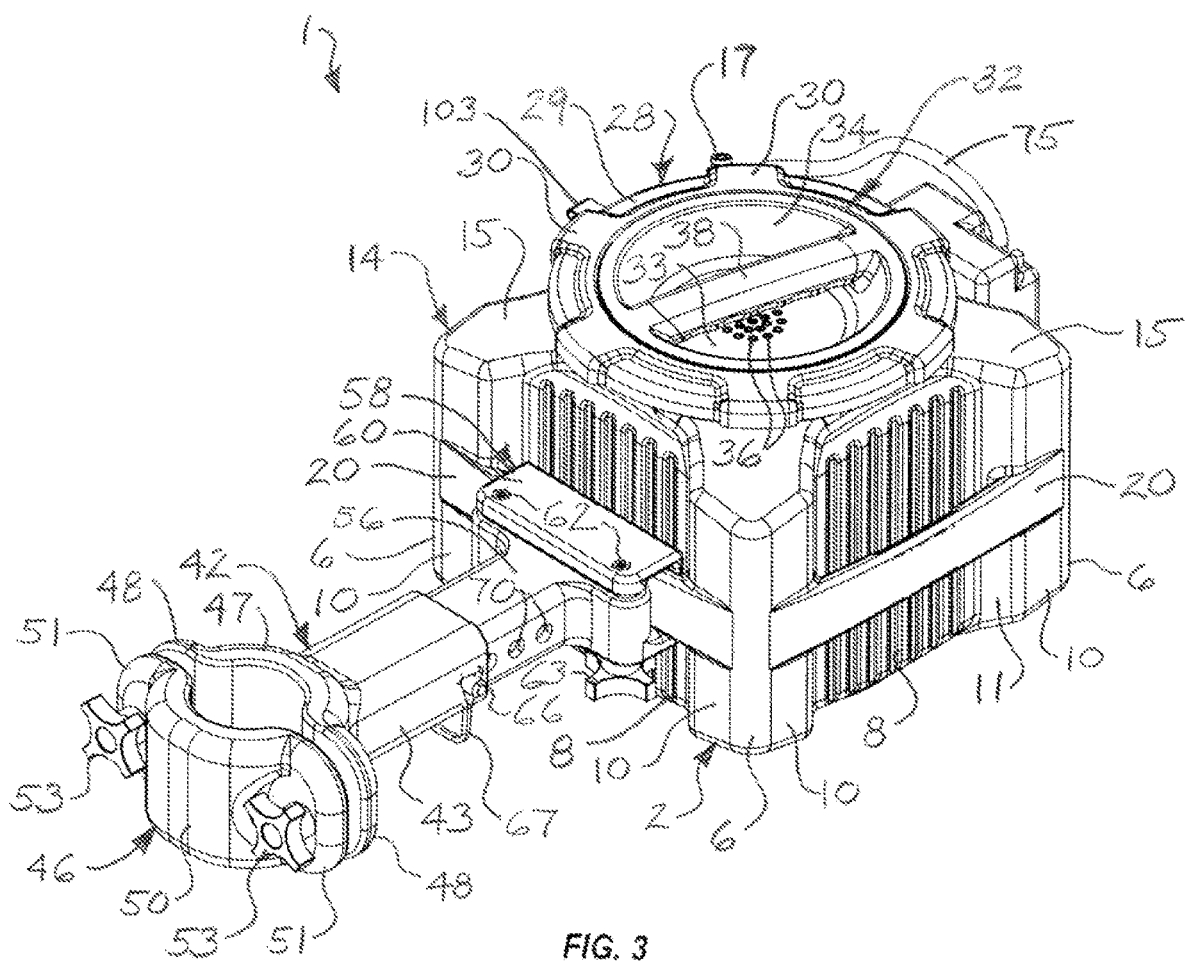
FIG. 3 is a right rear perspective view of the illustrative live bait container assembly.
Figure 4:
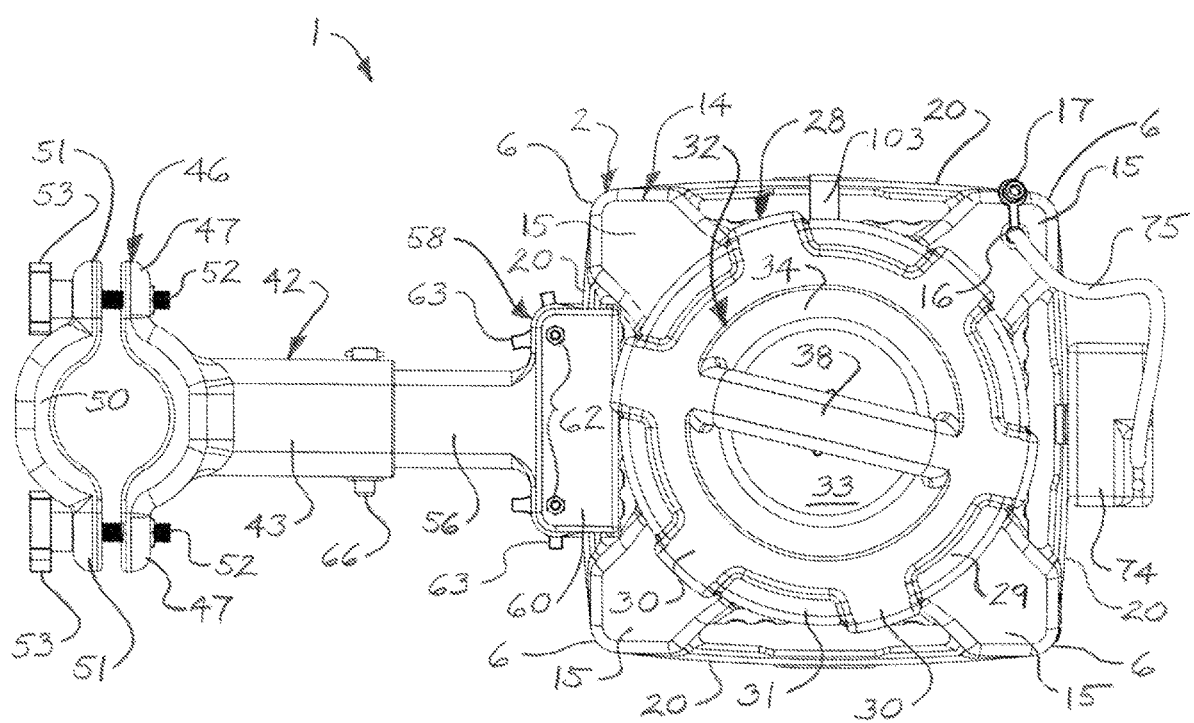
FIG. 4 is a top view of the illustrative live bait container assembly.

As illustrated in FIG. 2, in some embodiments, at least one aerator opening 16 may be provided in the bait container 2 in communication with the container interior 24. At least one aerator 74 may be provided on the exterior of the bait container 2. The aerator 74 may include a battery-operated aerator known by those skilled in the art. In some embodiments or applications, the aerator 74 may be mounted on a selected one of the container handles 20 using a bracket, clamp, mechanical fasteners and/or other suitable mounting technique (not illustrated). An aerator tube 75 may extend from the aerator 74, through the aerator opening 16 and into the container interior 24 for the purpose of aerating water (not illustrated) in the container interior 24 in typical application of the assembly 1, which will be hereinafter described. As illustrated in FIG. 1, an aerator opening cap 17 may close the aerator opening 16 when not in use.

Figure 12:
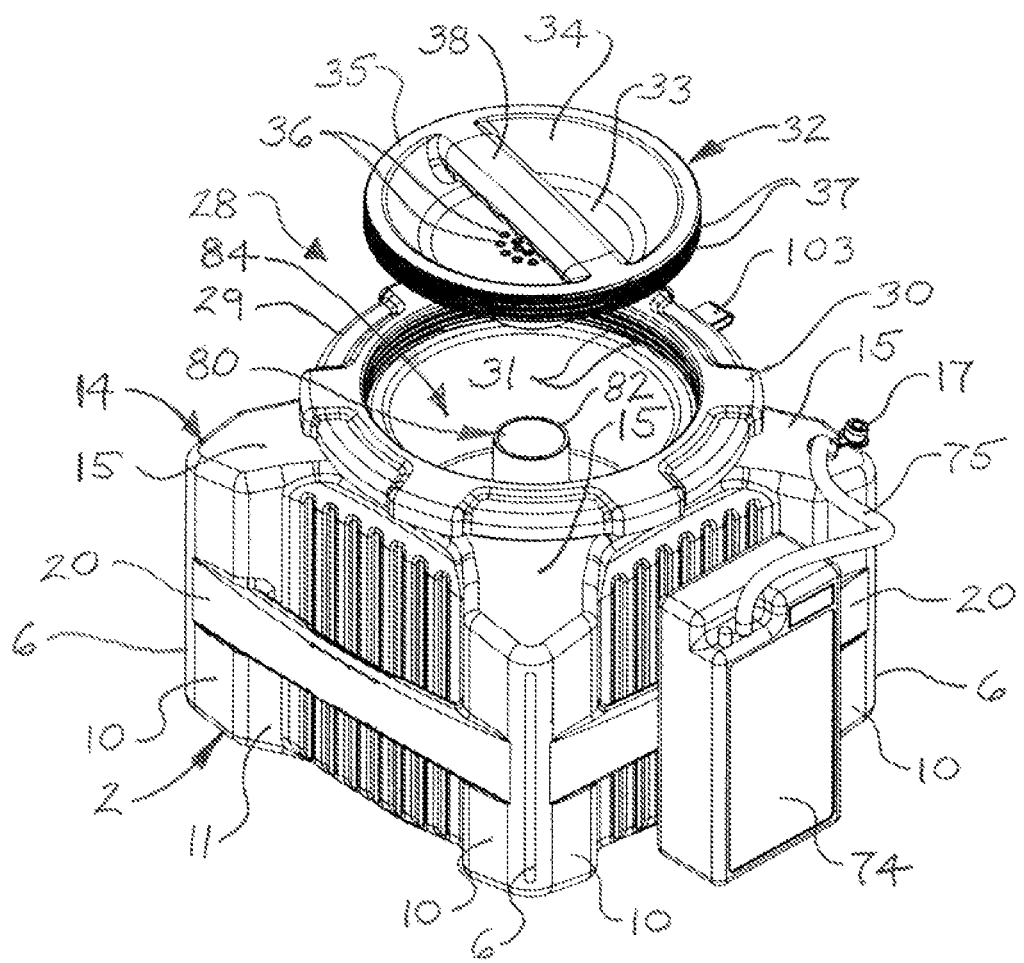
FIG. 12 is an exploded front perspective view of the bait container with an inner lid portion removed from a container lid rim of the container lid assembly to expose a worm insert deployed in the bait container.
Figure 15:
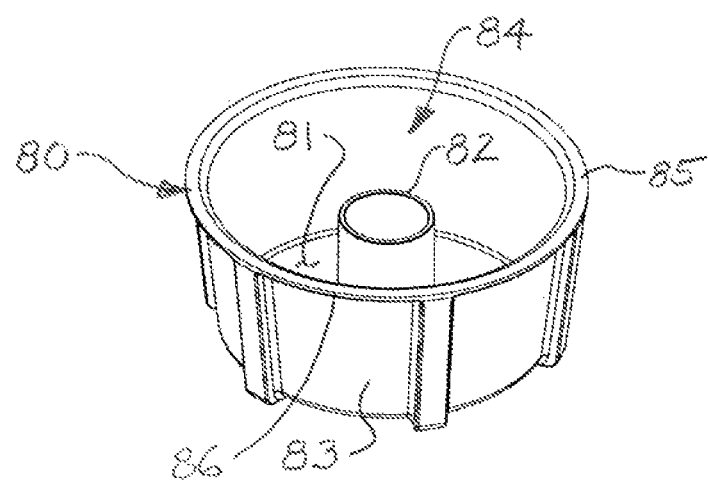
FIG. 15 is a perspective view of a typical worm insert.
Figure 16:
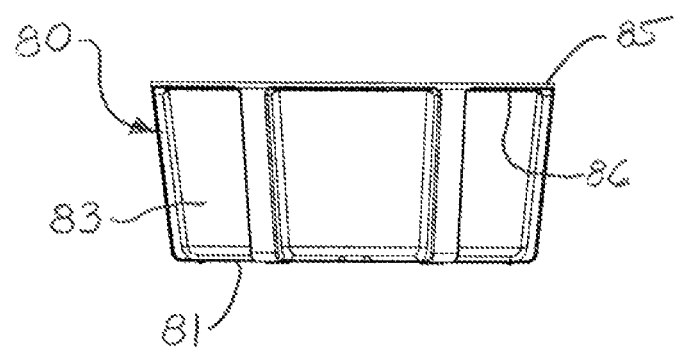
FIG. 16 is a side view of the worm insert.

A container lid assembly 28 may be provided on the bait container 2. As illustrated in FIG. 12, in some embodiments, the container lid assembly 28 may include an annular container lid rim 29. Grip flanges 30 may extend outwardly from the exterior circumference of the container lid rim 29 in spaced-apart relationship to each other. As illustrated in FIG. 9, multiple, spaced-apart ring retainer flanges 39 may extend outwardly from the container lid rim 29 around the interior circumference thereof for purposes which will be hereinafter described. In some embodiments, rim threads 31 may be provided on an interior surface of the container lid rim 29. The rim threads 31 may traverse substantially the entire interior circumference of the container lid rim 29 to provide sufficient threading for both attachment of the container lid rim 29 to the container neck 18 of the bait container 2 and attachment of the inner lid portion 32 to the container lid rim 29 of the container lid assembly 28. Accordingly, the container lid rim 29 may be selectively attached to the bait container 2 by engagement of the lower portion of the interior rim threads 31 in the container lid rim 29 with the companion exterior container neck threads 19 (FIG. 9) on the container neck 18 of the bait container 2 responsive to typically clockwise rotation of the container lid rim 29. The container lid rim 29 may be selectively removed from the bait container 2 typically by counterclockwise rotation of the container lid rim 29.

As further illustrated in FIG. 9, a hinge assembly 100 may attach or tether the container lid assembly 28 to the bait container 2 to facilitate pivoted opening and closing of the container lid assembly 28 on the bait container 2. In some embodiments, the hinge assembly 100 may include a neck ring 101 which may encircle the container neck 18 on the bait container 2. A lid ring 102 may be slidably retained between the container lid rim 29 and the ring retainer flanges 39 to facilitate rotation and unthreading and removal of the container lid rim 29 from the container neck 18. Accordingly, the container lid rim 29 may rotate with respect to the stationary lid ring 102 as the lid ring 102 slides between the rotating container lid rim 29 and the ring retainer flanges 39. An elongated, flexible lid hinge 103 of selected design may connect the lid ring 102 to the neck ring 101. In other embodiments, the hinge assembly 100 may be omitted and the container lid assembly 28 may be removed from the bait container 2 to expose the container interior 24 typically through the neck opening 22 of the container neck 18.

Figure 8:
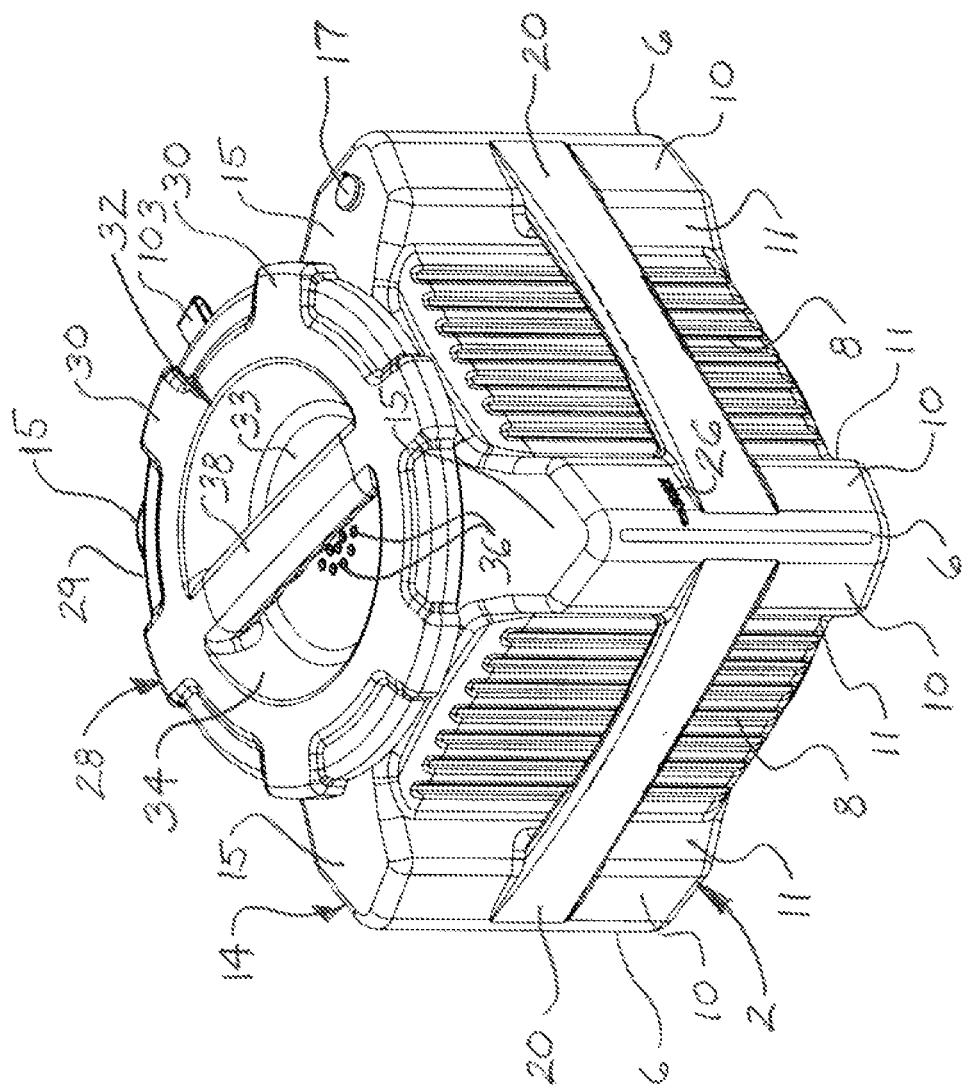
FIG. 8 is a perspective view of a typical bait container of the illustrative live bait container assembly with a container lid assembly shown in a closed position on the bait container.

An inner lid portion 32 may be provided in the container lid rim 29. In some embodiments, the inner lid portion 32 may detachably or removably engage the container lid rim 29 typically as will be hereinafter described. The inner lid portion 32 may be concave or dish-shaped with a bottom lid wall 33. A side lid wall 34 may angle from the bottom lid wall 33. A lid flange 35 may extend outwardly and downwardly from the side lid wall 34. As illustrated in FIG. 8, a container lid handle 38 may span the side lid wall 34. In some embodiments, at least one container lid opening 36 may extend through the bottom lid wall 33. As illustrated in FIG. 9, a lid baffle 40 may extend from the bottom or interior surface of the bottom lid wall 33 of the inner lid portion 32. The lid baffle 40 may be cylindrical and may circumscribe the container lid opening or openings 36 in the bottom lid wall 33. Accordingly, the lid baffle 40 may block and prevent or minimize splashing of water from the container interior 24 through the container lid openings 36 during sudden or inadvertent movement of the bait container 2.

The inner lid portion 32 may detachably engage the container lid rim 29 of the container lid assembly 28 according to the knowledge of those skilled in the art. Accordingly, as illustrated in FIG. 12, in some embodiments, exterior lid threads 37 may be provided on the lid flange 35 of the inner lid portion 32. The exterior lid threads 37 may be configured to detachably engage or mesh with the upper portion of the companion interior rim threads 31 in the container lid rim 29 to removably secure the inner lid portion 32 in the container lid rim 29 as the container lid rim 29 typically remains attached to the container neck 18 of the bait container 2 and the lower portion of the interior rim threads 31 remains in engagement with the exterior container neck threads 19 (FIG. 9) on the container neck 18. As further illustrated in FIG. 12, the inner lid portion 32 may thus be deployed in place in the container lid rim 29 by engagement of the exterior lid threads 37 on the lid flange 35 of the inner lid portion 32 typically with the upper portion of the companion interior rim threads 31 in the container lid rim 29 as the inner lid portion 32 is rotated typically in the clockwise direction with respect to the container lid rim 29. The inner lid portion 32 may be selectively disengaged and removed from the container lid rim 29 typically by counterclockwise rotation of the inner lid portion 32 in the container lid rim 29. The container lid rim 29, inner lid portion 32, hinge assembly 100 and other components of the container lid assembly 28 may be molded, casted, machined and/or otherwise fabricated of plastic, composites, metals and/or other suitable materials.

In some embodiments, the arm assembly 42 of the assembly 1 may be selectively length-adjustable. Accordingly, the arm assembly 42 may include a proximal arm segment 56. A distal arm segment 43 may telescopically interface with the proximal arm segment 56. A selected length of the distal arm segment 43 may be selectively securable with respect to the proximal arm segment 56 according to the knowledge of those skilled in the art. Accordingly, as illustrated in FIGS. 3 and 5-7, in some embodiments, multiple, spaced-apart pin openings 70 may be provided in the proximal arm segment 56 along its length. A pin opening (not illustrated) may be provided in the distal arm segment 43. An arm adjustment pin 66 may be extended through the pin opening in the distal arm segment 43 and through a selected registering pin opening 70 in the proximal arm segment 56 to secure a selected length of the arm assembly 42. A pin lanyard 67 may attach or tether the arm adjustment pin 66 to the distal arm segment 43. The components of the arm assembly 42 may be molded, casted, machined and/or otherwise fabricated of plastic, composites, metals and/or other suitable materials.

The arm assembly 42 may be attached to the bait container 2 using any suitable technique known by those skilled in the art. As illustrated in FIGS. 3-7, in some embodiments, an arm clamp 58 may terminate the end of the proximal arm segment 56 which is opposite the distal arm segment 43. The arm clamp 58 may include a fixed clamp jaw 59 which may be fabricated in one piece with or fabricated separately and attached to the proximal arm segment 56 using fasteners, brackets, clamps and/or other suitable attachment technique. A movable clamp jaw 60 may be mounted in movable relationship to the fixed clamp jaw 59 according to the knowledge of those skilled in the art. As illustrated in FIG. 6, in some embodiments, at least one, and typically, a pair of spaced-apart jaw fasteners 62 may attach the movable clamp jaw 60 to the fixed clamp jaw 59. The jaw fasteners 62 may threadably engage a pair of respective fastener openings (not illustrated) which extend through the movable clamp jaw 60. A pair of fastener handles 63 may engage the respective jaw fasteners 62 for rotation within the respective fastener openings. Accordingly, the fastener handles 63 may be selectively rotated in a first direction with the respective jaw fasteners 62 to threadably engage the fastener openings and facilitate movement of the movable clamp jaw 60 away from the fixed clamp jaw 59. The fastener handles 63 with the jaw fasteners 62 may be rotated in a second direction to move the movable clamp jaw 60 toward the fixed clamp jaw 59. Thus, the fastener handles 63 may be rotated to open the arm clamp 58 and facilitate placement of a selected one of the container handles 20 on the bait container 2 between the fixed clamp jaw 59 and the movable clamp jaw 60 and then rotated to close the arm clamp 58 and secure the fixed clamp jaw 59 and the movable clamp jaw 60 against the container handle 20. It will be recognized and understood that the arm clamp 58 represents a non-limiting example of a mechanism which is suitable for the purpose of mounting the bait container 2 on the arm assembly 42 and that alternative mechanisms which are known by those skilled in the art and suitable for the purpose may be used instead of or in addition to the arm clamp 58.

The arm assembly 42 may be configured for attachment to the seat pedestal 96 (FIGS. 21-23) of the watercraft seat 95 according to any suitable technique which is known by those skilled in the art. In some embodiments, an arm mount collar 46 may be provided on the distal arm segment 43 for the purpose. The arm mount collar 46 may include a generally semicircular or curved fixed collar segment 47 which terminates the end of the distal arm segment 43 which is opposite the proximal arm segment 56. A pair of spaced-apart, fixed collar segment flanges 48 may terminate opposite ends of the fixed collar segment 47. A complementary, generally semicircular or curved removable collar segment 50 may include a pair of removable collar segment flanges 51 which may be secured to the respective fixed collar segment flanges 48 of the fixed collar segment 47 typically using a respective pair of collar fasteners 52. Each collar fastener 52 may threadably engage a corresponding fastener opening (not illustrated) which extends through each corresponding fixed collar segment flange 48 of the fixed collar segment 47. A pair of fastener handles 53 may engage the respective collar fasteners 52 to facilitate selective rotation of the collar fasteners 52 in a first direction for loosening of the removable collar segment 50 relative to or removal of the removable collar segment 50 from the fixed collar segment 47 and selective rotation of the collar fasteners 52 in a second direction for tightening of the removable collar segment 50 relative to the fixed collar segment 47.

Referring next to FIGS. 21-23 of the drawings, in typical application of the assembly 1, a supply of water (not illustrated) may be poured in or otherwise placed into the container interior 24 of the bait container 2. This may be accomplished typically by unthreading and removing the inner lid portion 32 from the container lid rim 29 of the container lid assembly 28 or by unthreading and removing the container lid rim 29 from the container neck 18 (FIG. 9) of the bait container 2. In some applications, the water may be poured into the container interior 24 through the neck opening 22 of the container neck 18 until the level of water reaches the maximum fill line 26 on the bait container 2. Minnows (not illustrated) and/or other live bait may be poured into the container interior 24 with the water or may be placed in the water after it is poured into the container interior 24. The inner lid portion 32 may then be replaced in the container lid rim 29 or the container lid rim 29 again threaded onto the container neck 18.

At least one aerator 74 may be attached typically to one of the container handles 20 of the bait container 2 such as by using a bracket, clamp, mechanical fasteners and/or other suitable mounting technique (not illustrated). The aerator tube 75 may be connected to the aerator 74 and inserted through the aerator opening 16 into the water in the container interior 24. The aerator 74 may be operated typically in the conventional manner to aerate the water in the container interior 24 through the aerator tube 75.

The arm assembly 42 may be attached to one of the container handles 20 on the bait container 2 such as by engagement of the arm clamp 58 on the proximal arm segment 56 with the container handle 20, typically as was heretofore described with respect to FIGS. 3-7. The arm assembly 42 may be attached to the seat pedestal 96 on the watercraft seat 95 of the watercraft 94 typically as illustrated in FIGS. 22 and 23. Accordingly, the collar fasteners 52 may initially be rotated and unthreaded from the respective fastener openings (not illustrated) in the fixed collar segment flanges 48 of the fixed collar segment 47, typically by counterclockwise rotation of the respective fastener handles 53, to disengage and remove the removable collar segment flanges 51 from the respective fixed collar flanges 48. The fixed collar segment 47 and the detached removable collar segment 50 may then be placed on opposite sides of the seat pedestal 96, after which the collar fasteners 52 may again be inserted and threaded into the respective fastener openings in the respective fixed collar segment flanges 48 and tightened, typically by clockwise rotation of the fastener handles 53, to secure the fixed collar segment 47 and the removable collar segment 50 around the seat pedestal %. The container bottom panel 3 of the bait container 2 typically rests on the watercraft floor 97 of the watercraft 94 in front of, adjacent to or behind the watercraft seat 95 depending typically on the preferences of the user. The typically flat, square or rectangular shape and low center of gravity of the bait container 2 may prevent the bait container 2 from inadvertently turning over and spilling water and live bait contents during wave action, travel or other movement of the watercraft 94 on a body of water. The arm assembly 42 may additionally secure or stabilize the bait container 2 during movement of the watercraft 94. Moreover, in some embodiments, the lid baffle 40 which may extend from the lower or interior surface of the bottom lid wall 33 may prevent or minimize splashing of water from the container interior 24 through the container lid openings 36 and into the inner lid portion 32. The typically dish-shaped concave configuration of the bottom lid wall 33 and side lid wall 34 of the inner lid portion 32 may further prevent accumulation of water in the inner lid portion 32, as any water which splashes from the container interior 24 through the container lid openings 36 falls back through the container lid openings 36 into the container interior 24.

As he or she sits on the watercraft seat 95, a user of the assembly 1 may access the live bait in the container interior 24 of the bait container 2, typically for fishing purposes, by unthreading and removing the inner lid portion 32 from the container lid rim 29 of the container lid assembly 28 and accessing the live bait through the neck opening 22 of the container neck 18. Alternatively, the container lid rim 29 may be unthreaded and removed from the container neck 18 of the bait container 2 and the live bait accessed through the neck opening 22. After the live bait is removed from the container interior 24, the inner lid portion 32 may be replaced in the container lid rim 29 or the container lid rim 29 may be replaced on the container neck 18. In some applications, crickets and/or other insects (not illustrated) may be placed in the container interior 24 for retrieval by removal of the inner lid portion 32 or container lid rim 29 of the container lid assembly 28.

In some applications, it may be desirous or advantageous to remove the bait container 2 from the assembly arm 42 as the assembly arm 42 remains attached to the seat pedestal 96 of the watercraft seat 95. This may be accomplished typically by opening the arm clamp 58 and disengaging the container handle 20 on the bait container 2 from the arm clamp 58. The bait container 2 may subsequently be reattached to the assembly arm 42 typically by reengagement of the container handle 20 with the arm clamp 58.

Referring next to FIGS. 12-16 of the drawings, in some applications, a worm insert 80 may be placed in the container interior 24 of the bait container 2. The worm insert 80 may be suitably configured to contain a supply of worms (not illustrated) and/or other live bait in water just beneath the inner lid portion 32 for case of access. As illustrated FIGS. 15 and 16, in some embodiments, the worm insert 80 may include bottom insert wall 81. An inner insert wall 82 and an outer insert wall 83 may extend from the bottom insert wall 81 in spaced-apart relationship to each other. A worm insert interior 84 may be formed by and between the bottom insert wall 81, the inner insert wall 82 and the outer insert wall 83. A worm insert edge 85 may extend around the outer insert wall 83. In some embodiments, exterior worm insert threads 86 may be provided on the worm insert edge 85. The worm insert threads 86 may be configured to engage the middle portion of the interior rim threads 31 (FIG. 12) of the container lid rim 29, typically between the lid threads 37 of the inner lid portion 32 and the container neck threads 19 on the container neck 18, in mounting or deployment of the worm insert 80 in the container lid assembly 28. In other embodiments, alternative techniques known by those skilled in the art may be used to support the worm insert 80 in the container interior 24. For example and without limitation, in some embodiments, an insert support shoulder (not illustrated) may protrude inwardly from the container neck 18 into the neck opening 22. The worm insert edge 85 may rest on the insert support shoulder. In still further embodiments, the worm insert edge 85 may threadably, frictionally and/or otherwise engage the interior surface of the lid flange 35 on the inner lid portion 32 or may engage the lid flange 35 through a cam-lock design, for example and without limitation. The worm insert 80 may be fabricated of plastic, composites, metals and/or other suitable materials according to the knowledge of those skilled in the art.

As illustrated in FIG. 14, when the container lid assembly 28 is deployed in place on the bait container 2, the worm insert 80 may extend into the container interior 24 with the inner insert wall 82 of the worm insert 80 typically extending into the lid baffle 40 of the inner lid portion 32 of the container lid assembly 28. The inner lid portion 32 can be selectively rotated and unthreaded and removed from the container lid rim 29 as the container lid rim 29 typically remains in place on the bait container 2 to facilitate placement of water with worms and/or other live bait (not illustrated) in the worm insert interior 84, and then replaced in the container lid rim 29. The worms and/or other live bait can be selectively accessed from the inner lid portion 32 typically by removal of the inner lid portion 32 from the container lid rim 29 in like manner.

Figures 17, 18:
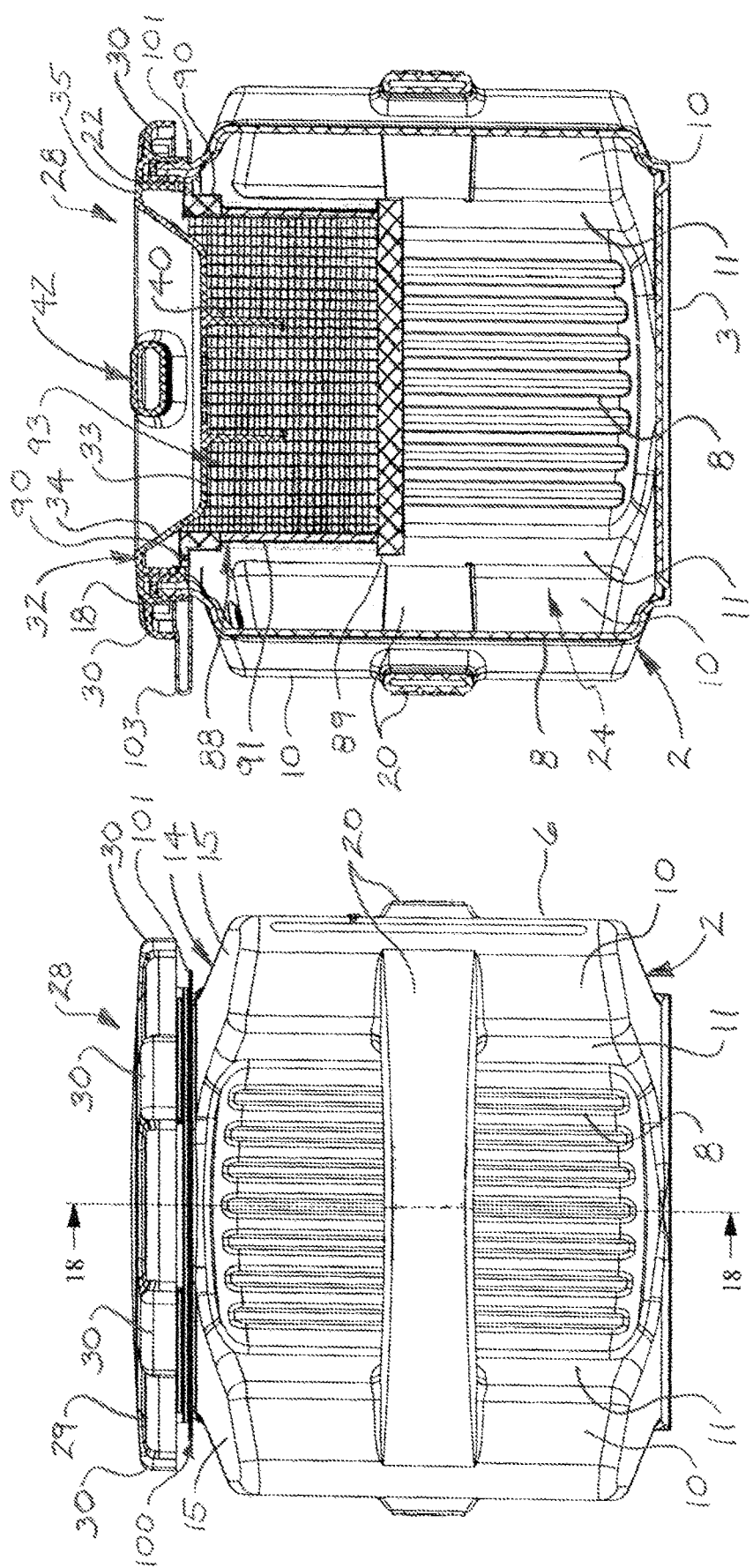
FIG. 17 is a rear view of the bait container with the container lid assembly in the closed position and with a cricket insert (not illustrated) disposed therein.
FIG. 18 is a cross-sectional view, taken along section lines 18-18 in FIG. 17, of the bait container with the cricket insert deployed in place therein.
Figure 19:
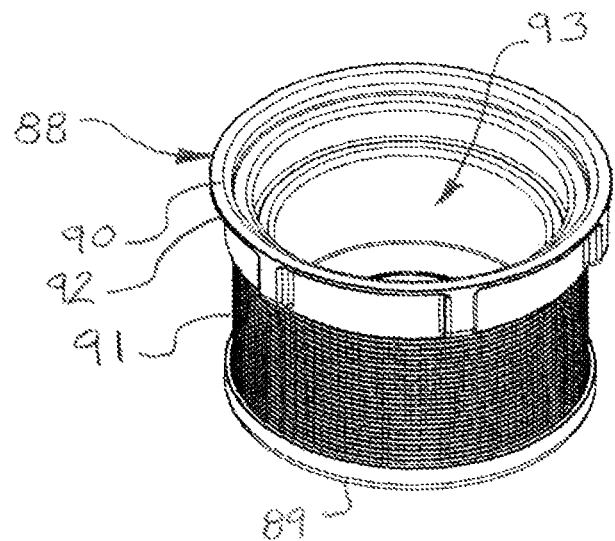
FIG. 19 is a perspective view of a typical cricket insert.
Figure 20:
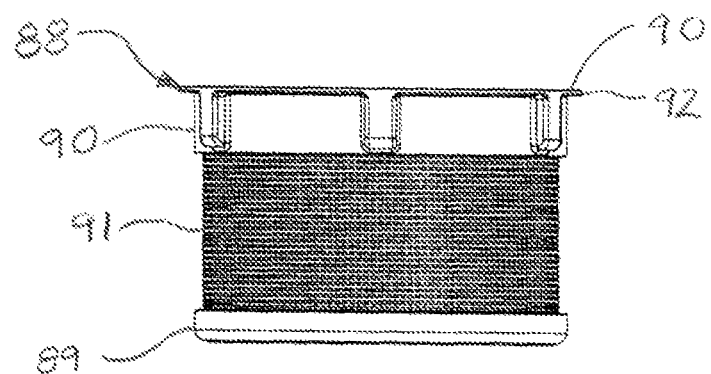
FIG. 20 is a side view of the cricket insert.

Referring next to FIGS. 17-20 of the drawings, in some applications, a cricket insert 88 may be placed in the container interior 24 of the bait container 2. The cricket insert 88 may be suitably configured to contain crickets (not illustrated) and/or other insects for use as live bait. The cricket insert 88 may include a cricket insert base 89 and a cricket insert rim 90 disposed in spaced-apart relationship to the cricket insert base 89. A cricket insert screen 91 may extend between the cricket insert base 89 and the cricket insert rim 90. A cricket insert interior 93 may be formed by and between the cricket insert base 89 and the cricket insert screen 91. As illustrated in FIGS. 19 and 20, in some embodiments, cricket insert threads 92 may be provided on the cricket insert rim 90. The cricket insert threads 92 may be configured to engage the interior rim threads 31 (FIG. 12) of the container lid rim 29, typically between the lid threads 37 of the inner lid portion 32 and the container neck threads 19 on the container neck 18, in mounting or deployment of the cricket insert 88 in the container lid assembly 28. In other embodiments, alternative techniques known by those skilled in the art may be used to support the cricket insert 88 in the container interior 24. For example and without limitation, in some embodiments, an insert support shoulder (not illustrated) may protrude inwardly from the container neck 18 into the neck opening 22. The cricket insert rim 90 may rest on the insert support shoulder. In still further embodiments, the cricket insert rim 90 may threadably, frictionally and/or otherwise engage the interior surface of the lid flange 35 on the inner lid portion 32 or may engage the lid flange 35 through a cam-lock design, for example and without limitation. The cricket insert 88 may be fabricated of plastic, composites, metals and/or other suitable materials according to the knowledge of those skilled in the art.

As illustrated in FIG. 18, when the container lid assembly 28 is deployed in place on the bait container 2, the cricket insert 88 may extend into the container interior 24. The inner lid portion 32 of the container lid assembly 28 can be rotated and unthreaded and removed from the container lid rim 29 to facilitate placement of live crickets and/or other bait (not illustrated) in the cricket insert interior 93, and then the inner lid portion 32 replaced on the container lid rim 29. The crickets and/or other bait can be selectively accessed from the cricket insert 88 by removal of the inner lid portion 32 from the container lid rim 29 or by removal of the container lid rim 29 and inner lid portion 32 from the container neck 18.

In some applications, various accessories (not illustrated) such as a worm light, a dry box for a cell phone or wallet, a fishing rod holder or a shoulder strap or securing strap, for example and without limitation, may be attached or secured to one or more of the container handles 20 of the bait container 2. The accessories may be attached to the container handles 20 either directly or using any suitable attachment device or mechanism such as clips, clamps, brackets, mechanical fasteners or the like. In some applications, at least one securing strap (not illustrated) may be tied to at least one of the container handles 20 or extended between the container handle 20 and the corresponding recessed container side panel 8. The securing strap may be tied or extended around a rack (not illustrated) on an all-terrain vehicle (ATV) or other type of vehicle to secure the bait container 2 for transport. In some applications, a worm light may be attached to a container handle 20 to facilitate illumination of minnows in the container interior 24, worms in the worm insert 80 or crickets in the cricket insert 88 in a dark or semi-dark environment. A shoulder strap (not illustrated) may be attached to one of the container handles 20 to enable a user to carry the bait container 2 using the shoulder strap.

It will be appreciated by those skilled in the art that the worm insert 80 and the cricket insert 88 may be selectively removably and interchangeably disposed in the container interior 24 of the bait container 2, typically in the foregoing manner, depending on the particular live bait which the user desires to use. It will be further appreciated by those skilled in the art that the bait container 2 may be used alone to contain live bait or may be used in combination with the worm insert 80 or the cricket insert 88 to contain a combination of worms, minnows, crickets and/or other live bait depending on the type of live bait which is desired. For example and without limitation, in some applications, minnows may be contained in the container interior 24 as the worm insert 80 is deployed in the container lid assembly 28 typically as was heretofore described with respect to FIGS. 12-16 and contains a supply of worms. The minnows may be removed from the container interior 24, as desired, by unthreading the container lid rim 29 from the container neck 18 as the inner lid portion 32 typically remains in place in the container lid rim 29 and the worm insert 80 typically remains attached to the container lid rim 29. Accordingly, as the container lid assembly 28 is pivoted on or removed from the bait container 2 to the open position, as illustrated in FIG. 9, the worm insert 80 may remain attached to the container lid assembly 28 and the minnows in the container interior 24 can be accessed through the neck opening 22, after which the container lid assembly 28 may again be closed on the bait container 2. In other applications, the cricket insert 88 may be deployed in the container lid assembly 28 as was heretofore described with respect to FIGS. 17-20 and contains a supply of crickets. The crickets may be removed from the cricket insert 88, as desired, by unthreading and removal of the inner lid portion 32 from the container lid rim 29. The minnows may be removed from the container interior 24, as desired, by unthreading the container lid rim 29 from the container neck 18 as the inner lid portion 32 remains in place in the container lid rim 29 and the cricket insert 88 typically remains attached to the container lid rim 29. As the container lid assembly 28 is pivoted on or removed from the bait container 2 to the open position, as illustrated in FIG. 9, the cricket insert 88 may remain attached to the container lid assembly 28 and the minnows in the container interior 24 can be accessed through the neck opening 22, after which the container lid assembly 28 may again be closed on the bait container 2.

In some embodiments, cam-locking or alternative locking or fastening mechanisms or devices known by those skilled in the art may be used instead of the container neck threads 19 on the container neck 18, the rim threads 31 on the container lid rim 29 lid threads 37 on the inner lid portion 32.

While certain illustrative embodiments of the disclosure have been described above, it will be recognized and understood that various modifications can be made to the embodiments and the appended claims are intended to cover all such modifications which may fall within the spirit and scope of the disclosure.

What is claimed is:

1. A live bait container assembly for mounting on a seat pedestal of a watercraft seat on a watercraft, comprising:
   a bait container including:
   a container bottom panel;
   a plurality of container corners carried by the container bottom panel;
   a plurality of recessed container side panels extending between the plurality of container corners;
   a plurality of container handles extending between the plurality of container corners in spaced-apart relationship to the plurality of recessed container side panels, respectively;
   a container top panel carried by the plurality of container corners and the plurality of recessed container side panels;
   a container interior formed by the container bottom panel, the plurality of container corners, the plurality of recessed container side panels and the container top panel; and
   a container neck having a neck opening extending from the container top panel, the container neck communicating with the container interior; and
   a container lid assembly removably carried by the container neck and closing the neck opening, the container lid assembly including:
   a container lid rim detachably carried by the container neck;
   a dish-shaped inner lid portion detachably carried by the container lid rim, the inner lid portion comprises a bottom lid wall, a side lid wall angling from the bottom lid wall, a lid flange extending from the side lid wall, at least one container lid opening in the bottom lid wall and a lid baffle extending from the bottom lid wall and circumscribing the at least one container lid opening; and
   a container lid handle carried by the inner lid portion.

2. The live bait container assembly of claim 1 further comprising an aerator opening in the bait container, an aerator carried by the bait container and an aerator tube extending through the aerator opening and establishing fluid communication between the aerator and the container interior of the bait container.

3. The live bait container assembly of claim 1 further comprising a worm insert removably disposed in the container interior of the bait container, the worm insert including a bottom insert wall, an inner insert wall extending from the bottom insert wall and an outer insert wall extending from the bottom insert wall in spaced-apart relationship to the inner insert wall.

4. The live bait container assembly of claim 1 further comprising a cricket insert removably disposed in the container interior of the bait container, the cricket insert including an insert base, an insert rim spaced-apart from the insert base and an insert screen extending between the insert base and the insert rim.

5. The live bait container assembly of claim 1 further comprising an arm assembly detachably engaging one of the plurality of container handles.

6. The live bait container assembly of claim 5 wherein the arm assembly is length-adjustable.

7. The live bait container assembly of claim 1 further comprising a pair of beveled corner panels extending from each of the plurality of recessed container side panels and a pair of corner side panels extending between the pair of beveled corner panels, respectively, and each corresponding pair of the plurality of container corners.

8. A live bait container assembly for mounting on a seat pedestal of a watercraft seat on a watercraft, comprising:
   a bait container including:
   a container bottom panel;

a plurality of container corners carried by the container bottom panel;

a plurality of recessed container side panels extending between the plurality of container corners;

a plurality of container handles extending between the plurality of container corners in spaced-apart relationship to the plurality of recessed container side panels, respectively;

a container top panel carried by the plurality of container corners and the plurality of recessed container side panels;

a container interior formed by the container bottom panel, the plurality of container corners, the plurality of recessed container side panels and the container top panel; and a container neck having a neck opening extending from the container top panel;

a container lid assembly removably carried by the container neck and closing the neck opening, the container lid assembly including:

a container lid rim detachably carried by the container neck;

a dish-shaped inner lid portion detachably carried by the container lid rim, the inner lid portion including:
a bottom lid wall;
a side lid wall angling from the bottom lid wall;
a lid flange extending from the side lid wall;
at least one container lid opening in the bottom lid wall;
a lid baffle extending from the bottom lid wall and circumscribing the at least one container lid opening; and
a container lid handle carried by the inner lid portion; and an arm assembly detachably carried by a selected one of the plurality of container handles and configured for attachment to the seat pedestal, the arm assembly is length-adjustable and includes a proximal arm segment detachably attached to the selected one of the plurality of container handles and a distal arm segment telescopically engaging the proximal arm segment, the distal arm segment configured for attachment to the seat pedestal.

9. The live bait container assembly of claim 8 further comprising an aerator opening in the bait container, an aerator carried by the bait container and an aerator tube extending through the aerator opening and establishing fluid communication between the aerator and the container interior of the bait container.

10. The live bait container assembly of claim 8 further comprising a worm insert removably disposed in the container interior of the bait container, the worm insert including a bottom insert wall, an inner insert wall extending from the bottom insert wall and an outer insert wall extending from the bottom insert wall in spaced-apart relationship to the inner insert wall.

11. The live bait container assembly of claim 8 further comprising a cricket insert removably disposed in the container interior of the bait container, the cricket insert including an insert base, an insert rim spaced-apart from the insert base and an insert screen extending between the insert base and the insert rim.

12. The live bait container assembly of claim 8 further comprising an arm clamp carried by the proximal arm segment of the arm assembly and detachably engaging the selected one of the plurality of container handles and an arm mount collar carried by the distal arm segment of the arm assembly and configured for attachment to the seat pedestal.

13. The live bait container assembly of claim 8 further comprising a pair of beveled corner panels extending from each of the plurality of recessed container side panels and a pair of corner side panels extending between the pair of beveled corner panels, respectively, and each corresponding pair of the plurality of container corners.

14. The live bait container assembly of claim 8 wherein a width or distance between adjacent ones of the plurality of container corners is greater than a height or distance between the container bottom panel and the container top panel of the bait container.

15. A container lid assembly for removable attachment to a container, comprising:

a container lid rim configured to detachably engage the container;

a dish-shaped inner lid portion removably fitted into the container lid rim, the inner lid portion including:
a bottom lid wall;
a side lid wall angling from the bottom lid wall;
a lid flange extending from the side lid wall, the lid flange configured for removably engaging the container lid rim;
a container lid handle spanning the side lid wall;
at least one container lid opening in the bottom lid wall; and
a lid baffle extending from the bottom lid wall, the lid baffle circumscribing the at least one container lid opening.

16. The container lid assembly of claim 15 further comprising interior rim threads in the container lid rim, the interior rim threads configured to detachably engage exterior container neck threads on the container.

17. The container lid assembly of claim 16 further comprising exterior lid threads on the lid flange of the inner lid portion, the exterior lid threads detachably engaging the interior rim threads in the container lid rim.

18. The container lid assembly of claim 15 further comprising a worm insert and a cricket insert removably and interchangeably disposed in the container interior of the bait container, the worm insert and the cricket insert configured to removably engage at least one of the container lid rim and the lid flange of the inner lid portion.

* * * * *